(12) United States Patent
Van Citters et al.

(10) Patent No.: US 11,534,558 B2
(45) Date of Patent: Dec. 27, 2022

(54) BILATERAL HUMERAL GUIDE FOR INTRAOSSEOUS INFUSION

(71) Applicant: THE TRUSTEES OF DARTMOUTH COLLEGE, Hanover, NH (US)

(72) Inventors: Douglas W. Van Citters, Hanover, NH (US); Alexander H. Slocum, Jr., Lebanon, NH (US); Steven D. Reinitz, Minneapolis, MN (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 17/628,543

(22) PCT Filed: Jul. 17, 2020

(86) PCT No.: PCT/US2020/042654
§ 371 (c)(1),
(2) Date: Jan. 19, 2022

(87) PCT Pub. No.: WO2021/016122
PCT Pub. Date: Jan. 28, 2021

(65) Prior Publication Data
US 2022/0257875 A1 Aug. 18, 2022

Related U.S. Application Data

(60) Provisional application No. 62/876,570, filed on Jul. 19, 2019.

(51) Int. Cl.
*A61M 5/42* (2006.01)
*A61B 17/34* (2006.01)
*A61B 90/00* (2016.01)

(52) U.S. Cl.
CPC ......... *A61M 5/427* (2013.01); *A61B 17/3472* (2013.01); *A61B 2017/3407* (2013.01);
(Continued)

(58) Field of Classification Search
CPC ................. A61M 5/427; A61M 2210/083
See application file for complete search history.

(56) References Cited

U.S. PATENT DOCUMENTS 2,525,398 A * 10/1950 Collins ............... A61M 5/00
248/230.8
8,419,683 B2 4/2013 Miller et al.
(Continued)

OTHER PUBLICATIONS

"2017 The Science and Fundamentals of Intraosseous Vascular Access" (Teleflex) Nov. 1-3, 5-12, 14-20, 2017 (Nov. 2017), entire document < https://www.teleflex.com/global/clinical-Aresources/documents/EZ-10_ Science _Fundamentals_ MC-003266-Revl-1.pdf > (Year: 2017).*

(Continued)

*Primary Examiner* — Jenna Zhang
(74) *Attorney, Agent, or Firm* — Lathrop GPM LLP

(57) ABSTRACT

A bilateral humeral guide for intraosseous infusion includes a three-dimensional mirror symmetric shell configured to fit on either shoulder of a patient, the shell being symmetric about a plane bisecting an alignment hole configured to aid positioning of the shell on the shoulder by aligning the alignment hole on acromion of the shoulder, and two insertion-site indication holes symmetrically positioned on two opposite sides of the plane, the insertion-site indication holes including a left and a right hole each configured to indicate insertion sites for intraosseous infusion through the shell to a target region of a left or right humerus of the patient when the shell is positioned on the shoulder corresponding to the respective humerus.

16 Claims, 14 Drawing Sheets

(52) U.S. Cl.
CPC ............... *A61B 2090/3937* (2016.02); *A61M 2210/005* (2013.01); *A61M 2210/02* (2013.01); *A61M 2210/083* (2013.01)

(56) References Cited

U.S. PATENT DOCUMENTS

| | | |
|---|---|---|
| 2007/0084742 A1 | 4/2007 | Miller et al. |
| 2008/0140014 A1 | 6/2008 | Miller et al. |
| 2017/0020560 A1* | 1/2017 | Van Citters ........ A61B 17/3472 |
| 2017/0135722 A1 | 5/2017 | Ben-mocha et al. |
| 2022/0039831 A1* | 2/2022 | Gowda .............. A61B 17/3403 |

OTHER PUBLICATIONS

International Application No. PCT/US2020/042654; International Search Report and Written Opinion dated Nov. 5, 2020; 11 pgs.
"2017 The Science and Fundamentals of Intraosseous Vascular Access" (Teleflex) Nov. 1-3, 5-12, 14-20, 2017 (Nov. 2017), entire document < https://www.teleflex.com/global/clinical-Aresources/documents/EZ-10_ Science _Fundamentals_ MC-003266-Rev1-1.pdf >.

* cited by examiner

Table E1: Humerus and upper arm measurements

| Measurement | Source | N | Range | Mean |
|---|---|---|---|---|
| Top of humeral head to surgical neck | Bones | 42 | 3.9 - 5.7 cm | 4.7 cm |
| Acromion to surgical neck | Cadavers | 23 | 6 - 9 cm | 7.7 cm |
| Acromion to surgical neck | Literature review | 420 | -- | Male: 7.23 cm / Female: 6.87 cm |
| Acromion thickness | | 175 | -- | Male: 7.7 mm / Female: 6.7 mm |
| Subacromial space | | 519 | -- | Male: 10.2 mm / Female: 9.2 mm |
| Humeral head to greater tuberosity | | 42 | -- | Male: 7.4 mm / Female: 5.8 mm |
| Greater tuberosity to surgical neck | | 42 | -- | Male: 4.7 cm / Female: 4.7 cm |

FIG. 9

BILATERAL HUMERAL GUIDE FOR INTRAOSSEOUS INFUSION

CROSS-REFERENCE TO RELATED APPLICATIONS

The present application is a 35 U.S.C. § 371 filing of International Application No. PCT/US2020/042654 filed Jul. 17, 2020, which claims priority to U.S. Provisional Patent Application No. 62/876,570 filed Jul. 19, 2019. The entire contents of the aforementioned provisional patent application are incorporated herein by reference.

BACKGROUND

Intraosseous (IO) infusion is a method of vascular access used in emergency situations when intravenous (IV) access is not feasible. Fluids or medications are injected into the bone marrow, primarily through the tibia or humerus, and enter the vascular system directly. IO access has been shown to be an effective alternative to IV access and is more efficient than intramuscular access.

Originally, IO access was achieved exclusively through the use of manual needles. However, a new generation of semi-automatic IO devices are now more often used. Of all currently marketed devices, the EZ-IO Intraosseous Vascular Access System (Teleflex, Morrisville, N.C.) is most common and has been shown to have the greatest first-time insertion success rate and lowest mean insertion time. The EZ-IO access technique involves the use of a small, battery-run, power driver, which is able to easily penetrate the skin, tissue, and outer cortex of bone, to reach the marrow. The drill and needle are then removed, leaving a hub securely positioned in the bone. A catheter is secured to the hub, allowing the delivery of medicine, blood components, or other fluids.

IO access is most commonly used by emergency medical service (EMS) personnel in cases of cardiac arrest. Tibial placement is often preferred, since the tibia is away from center of body (where other resuscitation efforts occur), and the correct insertion site is relatively easy to palpate. However, some EMS providers prefer the humeral insertion site, because they believe that it achieves a better flow rate, due to its proximity to the heart. Additionally, cases of lower extremity trauma, bilateral knee replacement, and bilateral amputation necessitate the use of the humerus for IO access. Although humeral access is less common than tibial access, the procedure is still necessary in certain situations, and it is important that medical providers are comfortable with the technique.

The current state-of-the-art method for insertion site location for humeral IO infusion is palpation of the patient's shoulder, in order to locate the greater tubercle. The first step in the process is to adduct the patient's elbow and position the forearm across the abdomen, in order to internally rotate the humerus and move the tubercle into an anterior position. To identify the vertical line of insertion on the proximal humerus, one hand should be placed vertically with the outside edge over the axilla. The other hand should be placed vertically with the outside edge along the midline of the upper arm. The line on which the thumbs lie (midway between the axilla and the midline of the upper arm) is the vertical insertion line. Along this line, one can palpate up the humerus to the surgical neck, which will feel like a "golf ball on a tee". The insertion site is one to two centimeters above the point where the "golf ball" and "tee" meet.

SUMMARY

A bilateral humeral guide for intraosseous infusion includes a three-dimensional mirror symmetric shell configured to fit on either shoulder of a patient, the shell having symmetric about a plane bisecting an alignment hole configured to aid positioning of the shell on the shoulder by aligning the alignment hole on acromion of the shoulder, and two insertion-site indication holes symmetrically positioned on two opposite sides of the plane, the insertion-site indication holes including a left and a right hole each configured to indicate insertion sites for intraosseous infusion through the shell to a target region of a left or right humerus of the patient when the shell is positioned on the shoulder corresponding to the respective humerus.

BRIEF DESCRIPTION OF THE FIGURES

FIG. 9 illustrates measurements of multiple male and female humeri.

DETAILED DESCRIPTION OF EXEMPLARY EMBODIMENTS

While the tibial insertion site is relatively unaffected by patient-to-patient variation in musculature and adipose tissue, the same is not true of the humeral site. As a result, palpation can be difficult, even for trained professionals. Incorrect placement, which can lead to serious complications (e.g., poor flow rate, needle dislodgement, or extravasation), is one of the greatest causes of failure in IO access procedures.

Disclosed herein are bilateral humeral guides for intraosseous (IO) infusion. The disclosed guides are configured to be intuitive, safe, and accurate so as to allow emergency medical service (EMS) personnel to rapidly and accurately identify the correct humeral insertion site. The disclosed guides are bilateral with symmetrical holes acting to identify the insertion sites on either the left or right arm of the patient.

The disclosed guides may function as a guide for a semi-automatic IO drill. Certain embodiments of the disclosed guides are compatible with the EZ-IO Intraosseous Vascular Access System (Teleflex, Morrisville, N.C.) and some other intraosseous access systems.

Palpating the humeral insertion site for IO access can be difficult, leading to unintended incorrect placement of IO lines, incorrect placement can then lead to complications such as poor flow rate, needle dislodgement, or extravasation. This device is a needle placement guide for humeral IO access that is intuitive, safe, accurate, and compatible with the EZ-IO, and some other, devices.

Figure 1A:
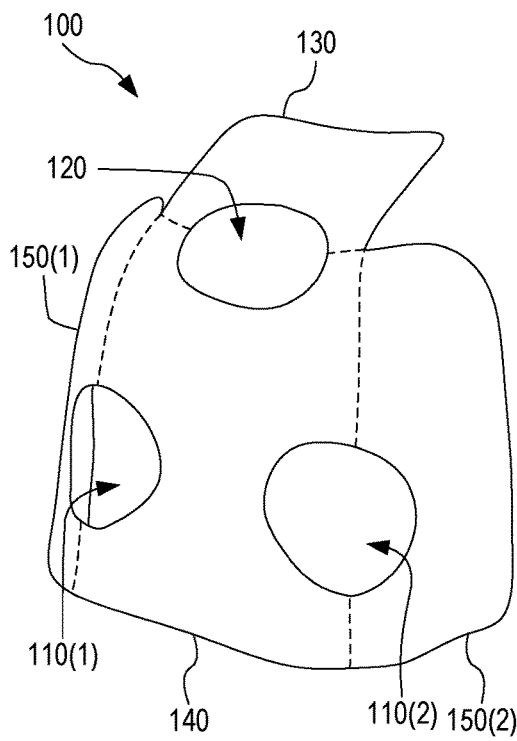
FIGS. 1A and 1B are perspective views of a bilateral humeral guide, In FIG. 2A, the guide is placed on the left shoulder of a patient, and in FIG. 2B, the guide is placed on the right shoulder of a patient.
Figure 1B:
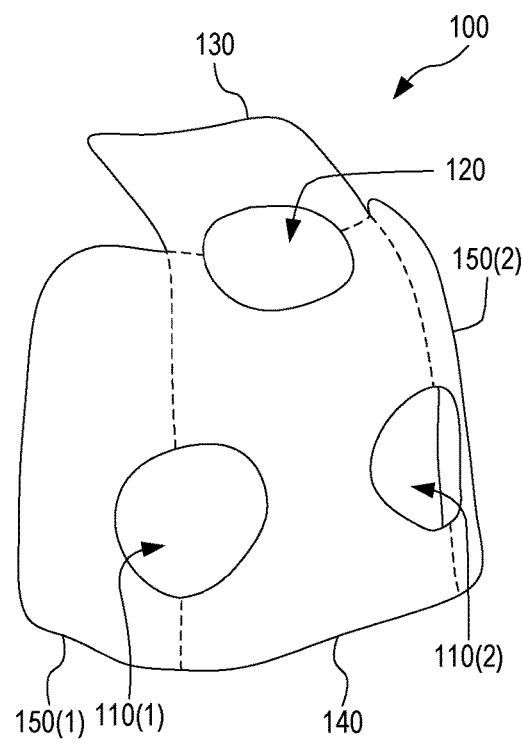
Figure 1C:
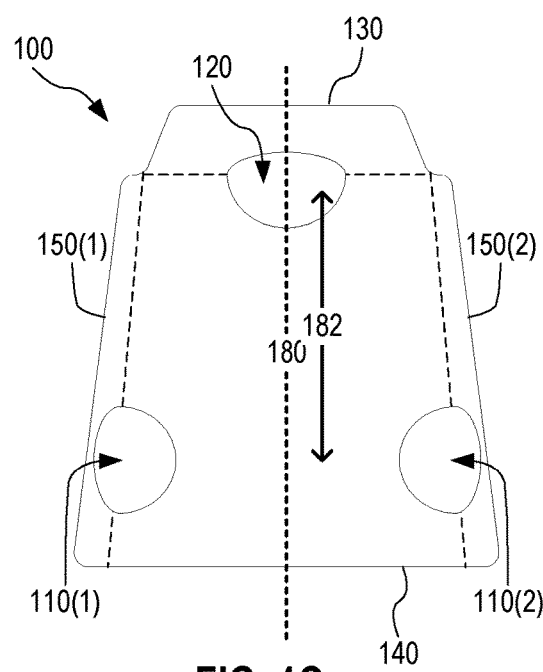
FIG. 1C is a lateral plan view of the guide of FIGS. 1A and 1B.
Figure 2A:
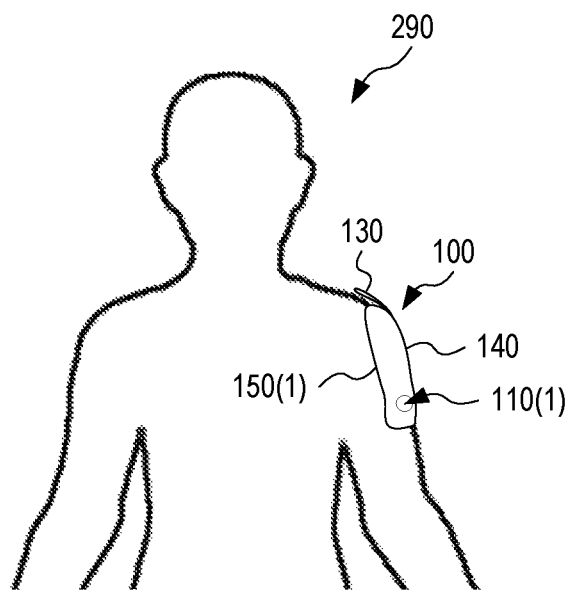
FIG. 2A, illustrates the guide of FIG. 1B placed on the right shoulder of a patient.
Figure 2B:
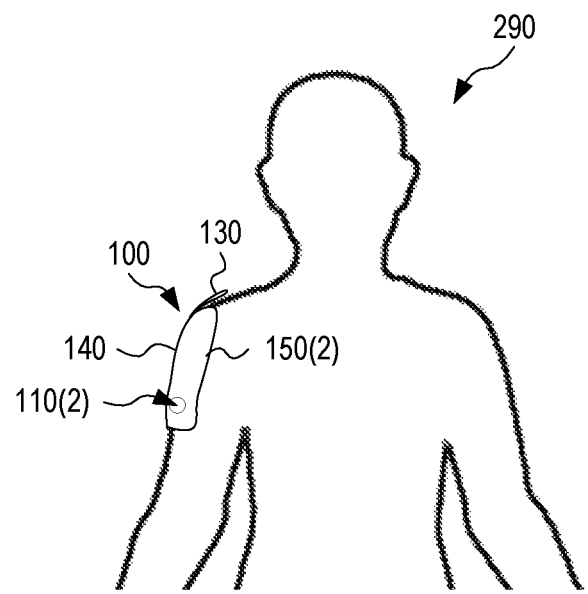
FIG. 2B illustrates the guide of FIG. 1A placed on the left shoulder of the patient.

FIGS. 1A-C illustrate one bilateral humeral guide 100 for IO infusion. FIGS. 1A and 1B are perspective views of guide 100, and FIG. 1C is a side plan view of guide 100. FIGS. 2A and 2B show the same guide 100 in two different use scenarios. In FIG. 2A, guide 100 is placed on the left shoulder of a patient 290. In FIG. 2B, guide 100 is placed on the right shoulder of patient 290. FIGS. 1A-C, 2A, and 2B are best viewed together in the following description.

Guide 100 is a three-dimensional shell shaped to fit in a cup-like fashion on either shoulder of patient 290. Guide 100 forms two insertion-site indication holes 110(1) and 110(2), and an alignment hole 120. Guide 100 is mirror symmetric with respect to reflection in a plane 180 (indicated by a dotted line in FIG. 1C), such that guide 100 works the same whether placed on the left or right shoulder of patient 290.

Alignment hole 120 is bisected by plane 180. Alignment hole 120 permits a user to use the acromion as a landmark for properly positioning guide 100 on the shoulder, so as to properly position one of insertion-site indication holes 110 relative to the humerus. By virtue of the mirror symmetry of guide 100 and by virtue of alignment hole 120 being centered relative to plane 180, the single alignment hole 120 works for both the left and the right shoulder. After initially placing guide 100 on the shoulder, a user palpates the shoulder through alignment hole 120 to locate the acromion and adjust the positioning of guide 100 as needed to make sure that guide 100 is properly positioned on the shoulder. Unlike the surgical neck of the humerus, the acromion is palpable across almost all patients, even those with increased muscle and/or adipose tissue. The acromion is therefore an appropriate and relatively fail-safe landmark for locating guide 100.

Insertion-site indication holes 110(1) and 110(2) are symmetrically positioned on two opposite sides, respectively, of plane 180. Each of insertion-site indication holes 110(1) and 110(2) is configured to provide IO access through guide 100 to a target region of a respective humerus when guide 100 is fit on the corresponding shoulder. In one set of scenarios, insertion-site indication hole 110(1) is intended to be used for IO access to the left humerus when guide 100 is fit on the left shoulder of patient 290 (as depicted in FIG. 2A), and insertion-site indication hole 110(2) is intended to be used for IO access to the right humerus when guide 100 is fit on the right shoulder of patient 290 (as depicted in FIG. 2B). In this set of scenarios, a user may use guide 100 to guide humeral IO infusion from an anterior-lateral direction, for example when patient 290 is in supine position or sitting in a chair.

Guide 100 may be integrally formed. In one example, guide 100 is injection molded. In an alternative embodiment, guide 100 is vacuformed from heat-softened sheet plastic. Guide 100 may be made of a material that has sufficient flexibility to conform to shoulders of a range of sizes and shapes, e.g., with a range of muscle and/or adipose tissue. Guide 100 is for example made of a polymer such as acrylonitrile butadiene styrene (ABS), nylon, polycarbonate (PC), polystyrene (PS), or a combination thereof. ABS, nylon, PC, and PS are advantageous because these materials are characterized by (a) a suitable Young's modulus to provide sufficient flexibility to conform to shoulders having a range of sizes and shapes, (b) a sufficiently high yield strength to withstand the required handling, (c) low cost, and (d) sufficiently high melting temperature. ABS and PS are extremely similar materials, however, ABS is more durable. Compared to nylon and PC, ABS is more flexible, lighter, and cheaper and is intermediate in hardness. Thus, guide 100 may advantageously be made of ABS.

Guide 100 may be viewed as having a top portion 130, a side portion 140, and two front-back portions 150(1) and 150(2). It is understood that top portion 130, side portion 140, and front-back portions 150(1) and 150(2) may be different portions of a single, integrally formed part. It is further understood that gradual transitions may exist between adjacent ones of top portion 130, side portion 140, and front-back portions 150(1) and 150(2). Top portion 130 is bisected by plane 180 and configured to fit on top of the shoulder. Side portion 140 extends from top portion 130, is bisected by plane 180, and is configured to fit against a lateral side of an upper arm of patient 290. Front-back portions 150(1) and 150(2) extend from side portion 140 on two respective opposite sides of plane 180 and form a mirror image of each other with respect to reflection in plane 180. Each front-back portion 150 is configured to extend in a medial direction from side portion 140. When guide 100 is positioned on the left shoulder of patient 290, front-back portion 150(1) is toward the front of the upper arm of patient 290 and front-back portion 150(2) is toward the back of the upper arm of patient 290 (see FIG. 2A). When guide 100 is positioned on the right shoulder of patient 290, front-back portion 150(1) is toward the back of the upper arm of patient 290 and front-back portion 150(2) is toward the front of the upper arm of patient 290 (see FIG. 2B). In an embodiment, each of insertion-site indication holes 110 is at the transition between side portion 140 and a respective one of front-back portions 150. Alignment hole 120 may be at the transition between top portion 130 and side portion 140.

Front-back portions 150 may or may not be parallel to each other. In one embodiment, front-back portions 150 flare out such that the distance between front-back portions 150 increases with distance from side portion 140. Top portion 130 may be at an oblique angle to side portion 140, for example as shown in FIGS. 1A and 1B.

As shown in FIGS. 1A-C, a notch may exist between top portion 130 and each of front-back portions 150(1) and 150(2), such that top portion 130 is (a) in direct connection only with side portion 140 and (b) connected to front-back portions 150 only indirectly via side portion 140. Such notches between top portion 130 and front-back portions 150 may provide flexibility, e.g., to conform to a range of shoulder size and shape. In an alternative embodiment, guide 100 does not have such notches, and top portion 130 connects directly to front-back portions 150.

Without departing from the scope hereof, guide 100 may have spatially varying flexibility. For example, it may be possible to flex guide 100 between top portion 130 and side portion 140, while side portion 140, front-back portions 150, and the transition therebetween are rigid or less flexible than the transition between top portion 130 and side portion 140.

In the region superior to the surgical neck, the greater tubercle is a preferred target insertion site for humeral IO infusion. The greater tubercle is approximately one-centimeter superior to the surgical neck and is an attractively barren spot on the humerus. It is bordered superiorly by the subdeltoid bursa and the insertion sites of the supraspinatus, infraspinatus, and teres minor muscles. The insertion sites for these muscles and the bursa should be avoided when drilling or inserting a needle. The greater tubercle is medially bounded by the bicipital groove, which houses the long tendon of the biceps brachii. The brachial artery and the median nerve are situated medial to the bicipital groove and lesser tubercle. In order to prevent damage to the artery or nerve, the bicipital groove serves as the medial border of the target region.

More generally, the target region is defined inferiorly by the surgical neck, superiorly by the subdeltoid bursa and muscle insertion sites, and medially by the bicipital groove. Laterally, there is no definitive anatomic boundary or concern. The only obstacle when drilling/inserting a needle into the greater tubercle are the deltoid muscles.

Figure 3:
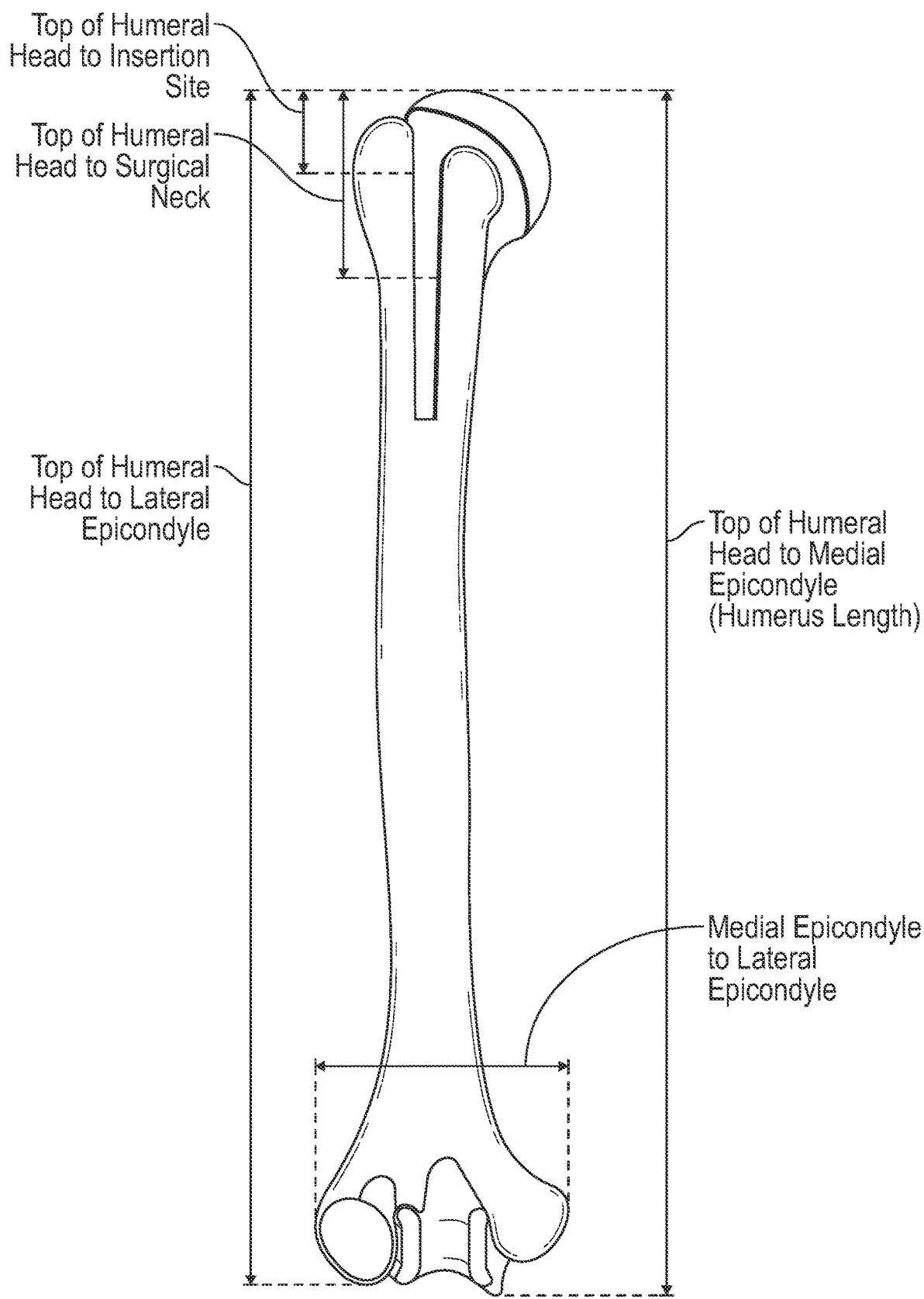
FIG. 3 illustrates a humerus bone showing landmarks on this bone.
Figure 4:
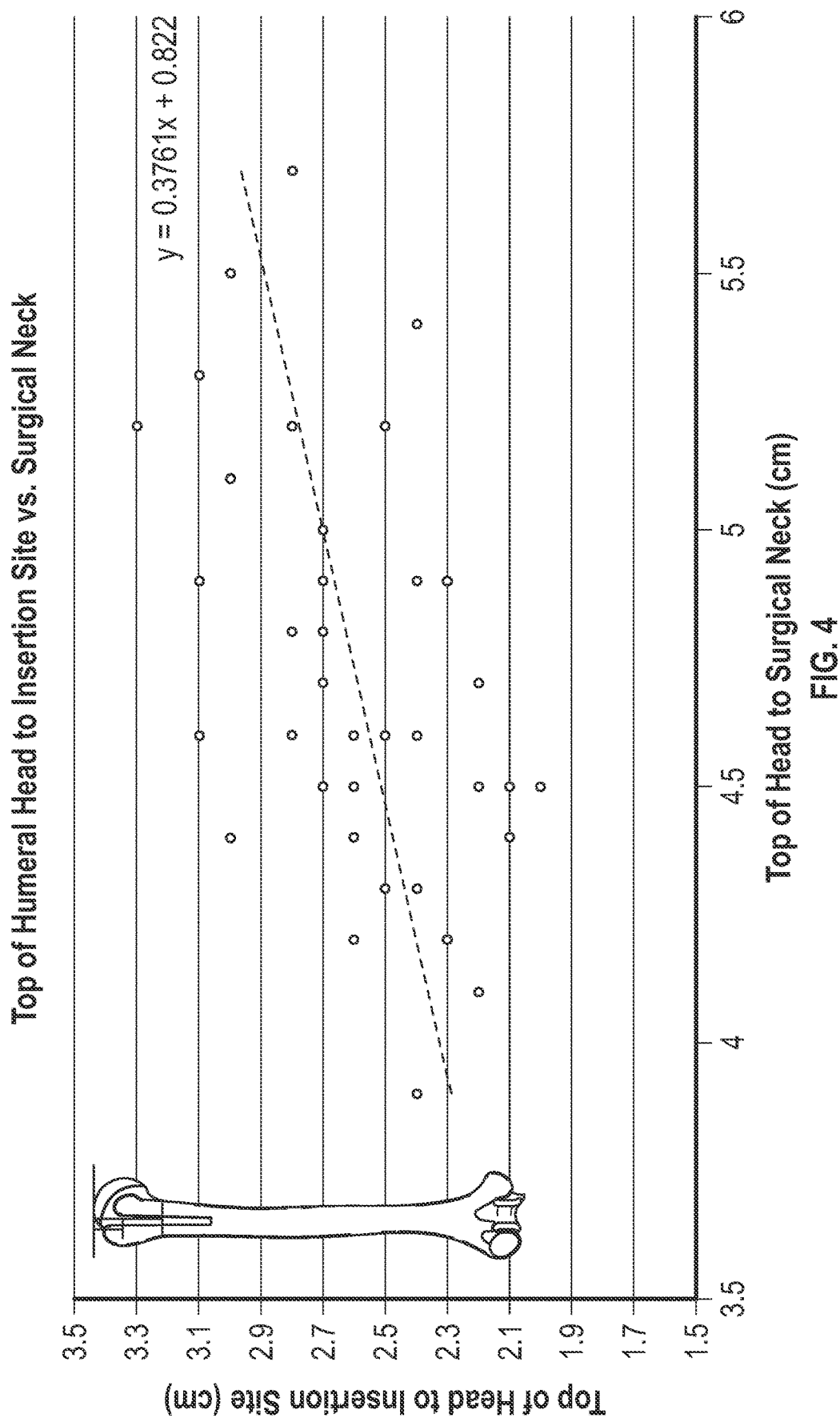
FIG. 4 illustrates measurements of multiple humeri from the top of the humeral head to the to a desired insertion site at the humeral neck.
Figure 5:
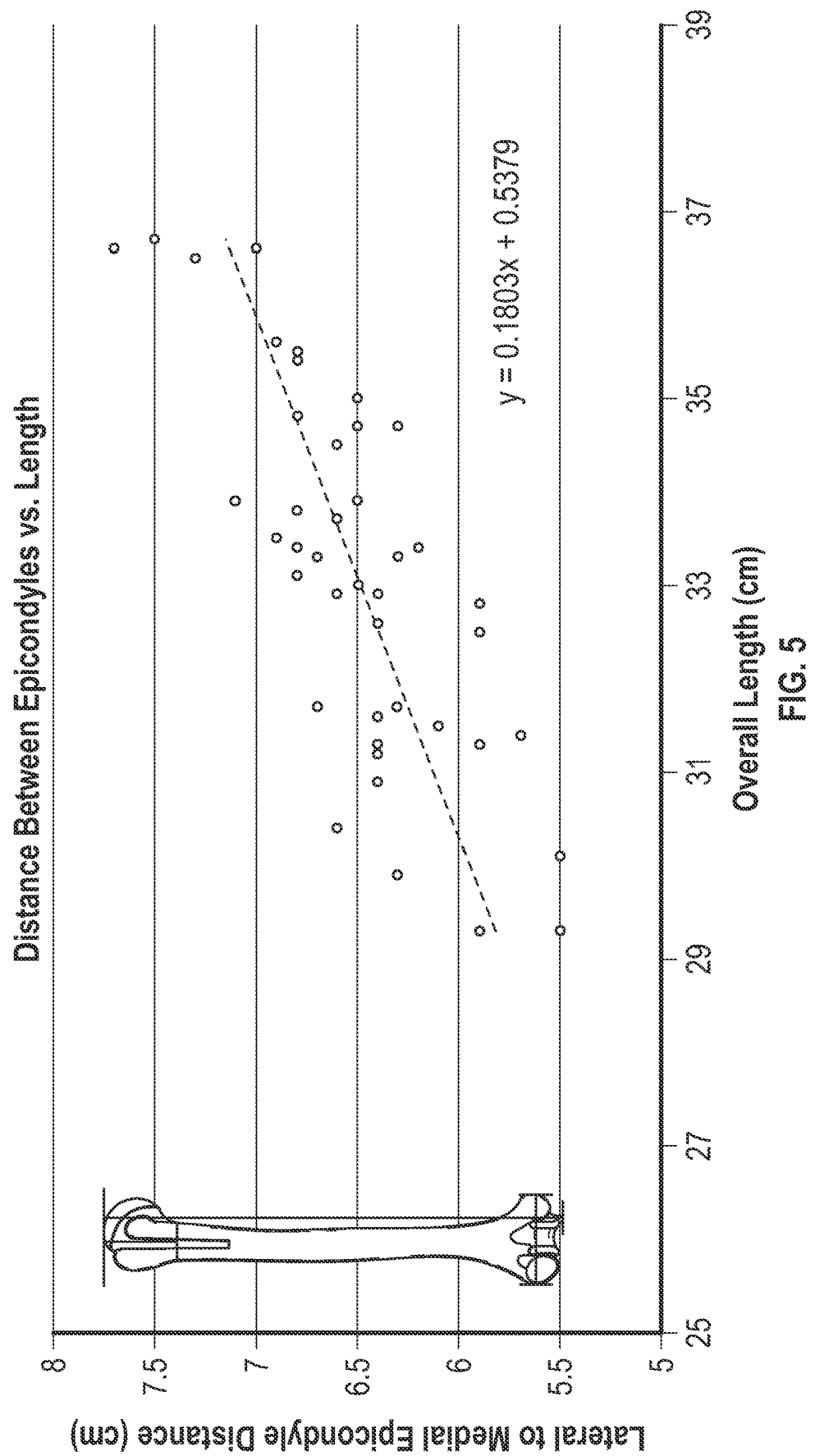
FIG. 5 illustrates measurements of multiple humeri from the lateral epicondyle to the medial epicondyle.
Figure 6:
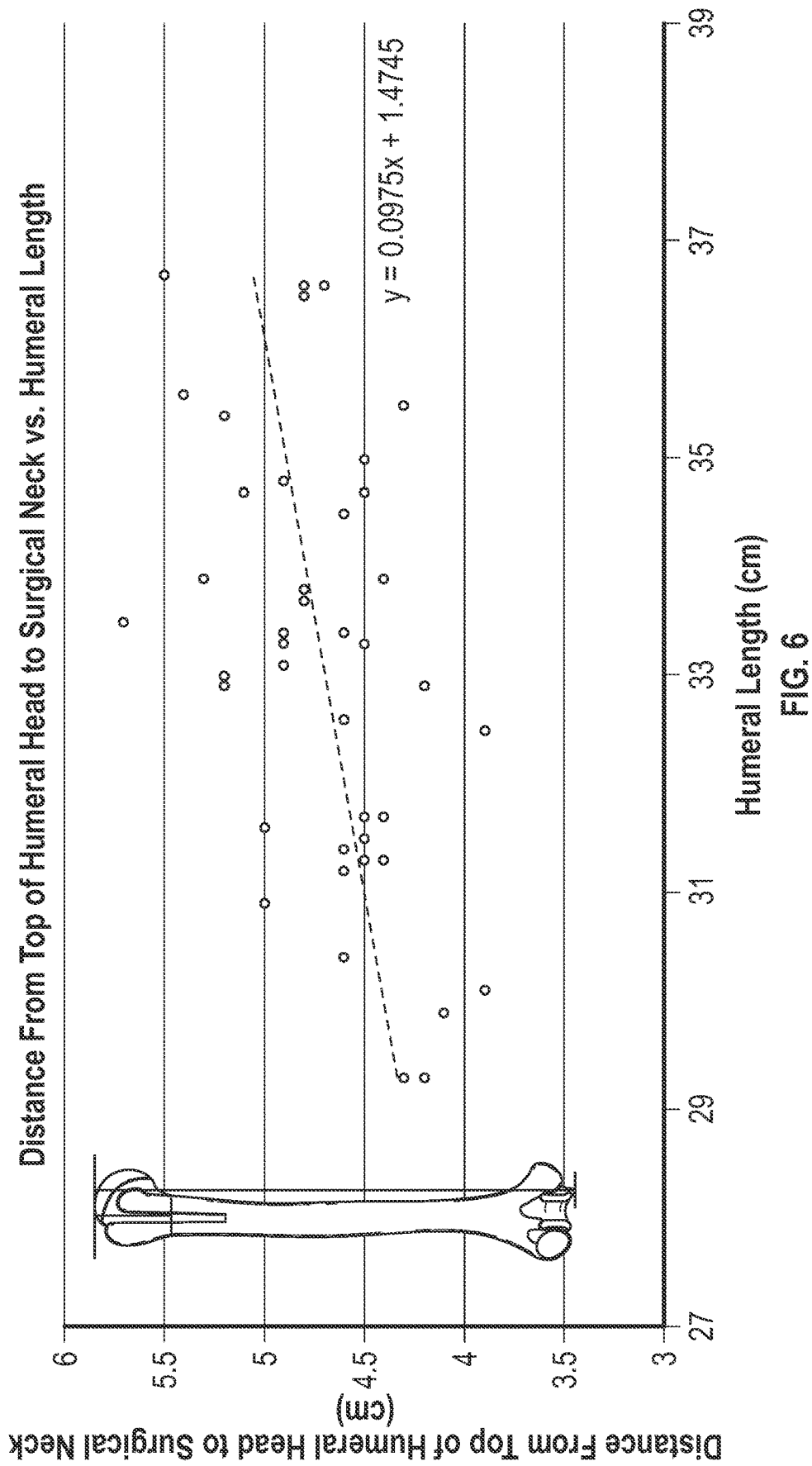
FIG. 6 illustrates measurements of multiple humeri including length to humeral head versus overall length.
Figure 7:
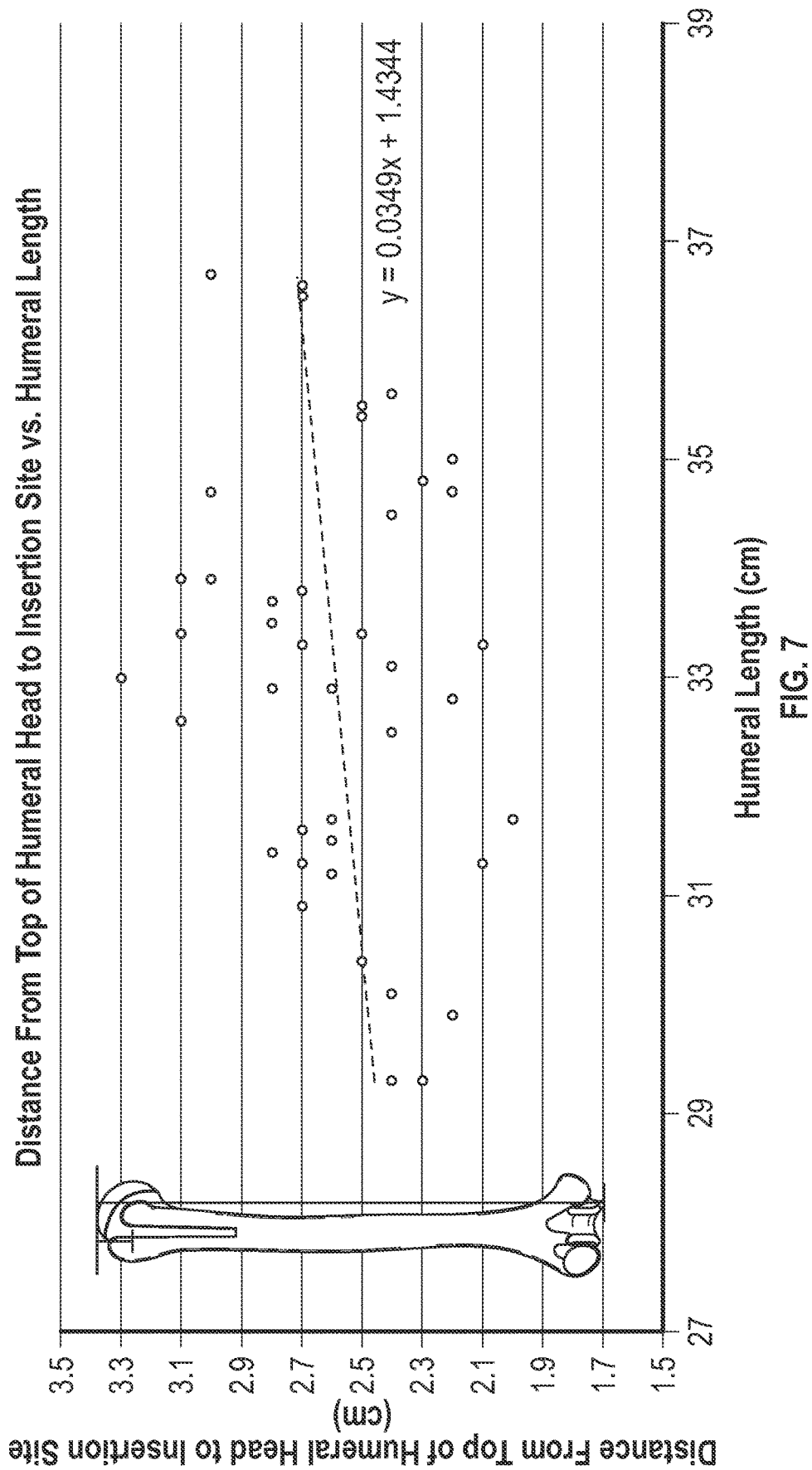
FIG. 7 illustrates measurements of multiple humeri including top of humeral head to a desired insertion site.
Figure 8:
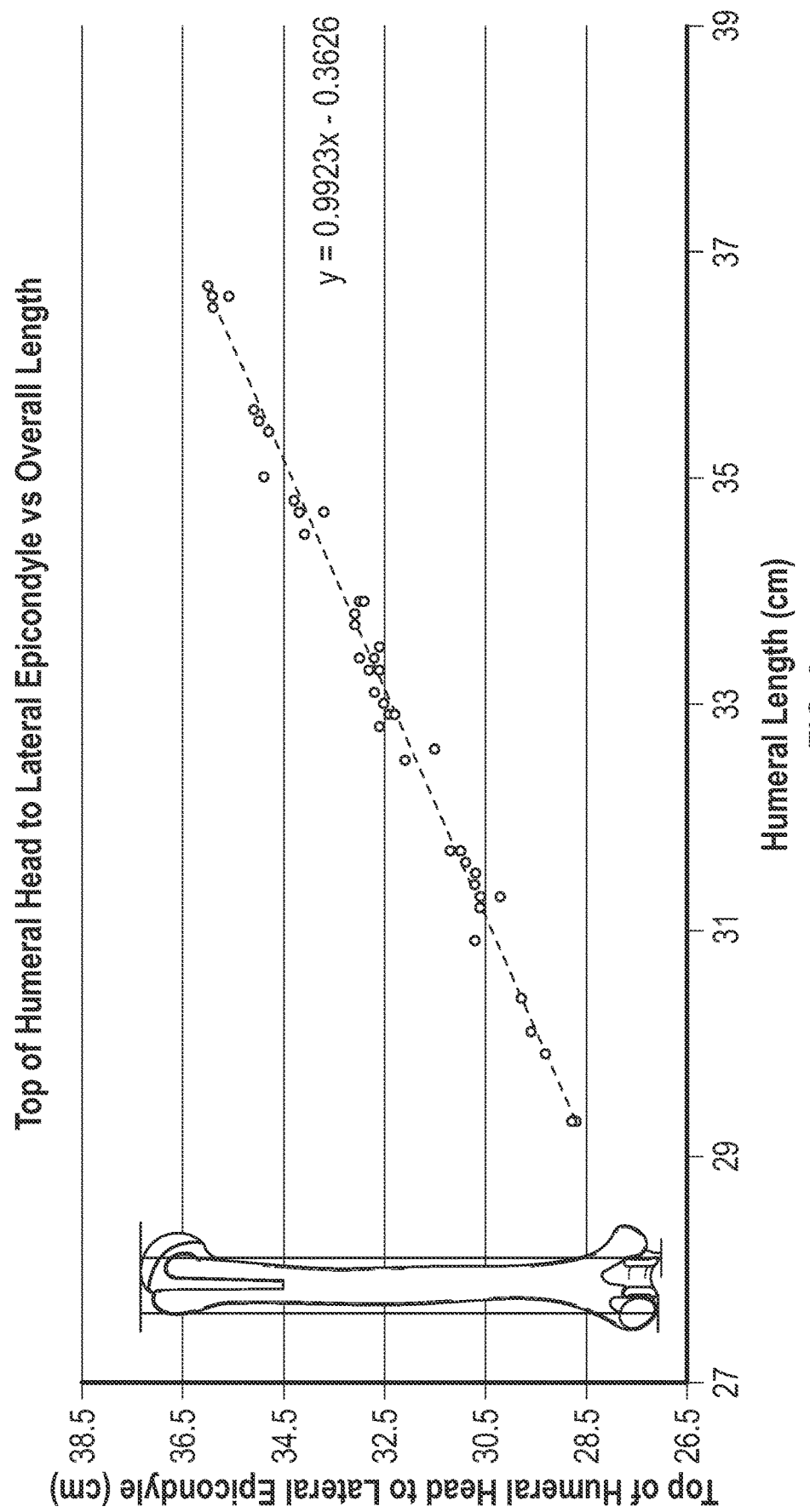
FIG. 8 illustrates measurements of multiple humeri including top of humeral head to lateral epicondyle versus overall length.
Figure 10:
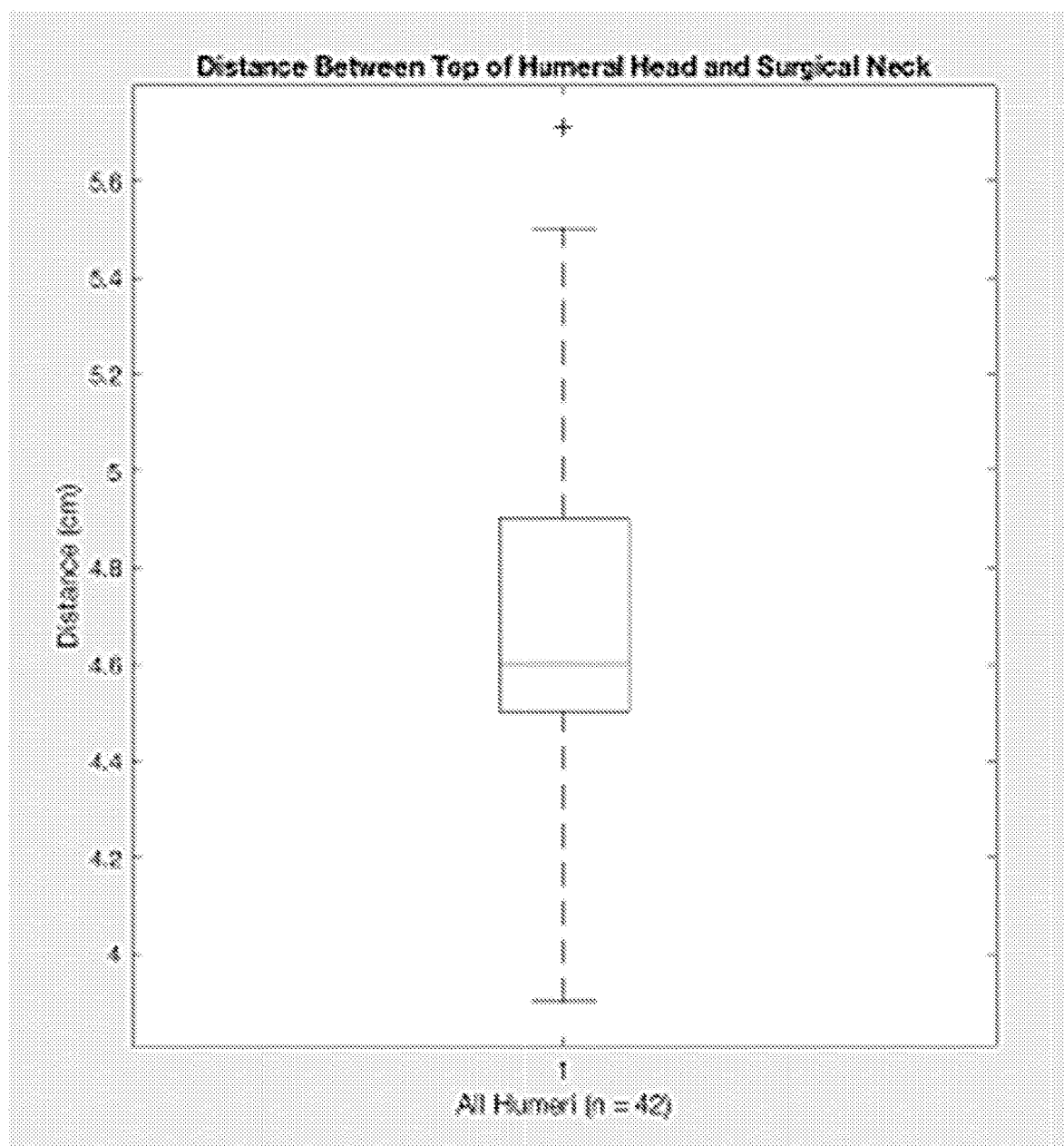
FIG. 10 illustrates a range of distances from the top of the humeral head to the surgical neck of multiple humeri.

In an effort to determine whether specific proportionalities exist in the humerus, human humeri were measured. Five measurements were taken for each bone (see FIG. 3), and linear regressions were performed on the data to test for correlations between the measurement points (see FIGS. 4-8). Measurements from the top of the humeral head to the surgical neck (a range encompassing the target region of interest) reveal that the variation between the largest distance and the smallest was under 2 centimeters (see FIGS. 9 and 10). Research also suggests limited variation (see FIG. 9). The measurements illustrated in FIGS. 4-10 validates the design of guide 100, which relies on minor variation in the proximal humerus.

Figure 11:
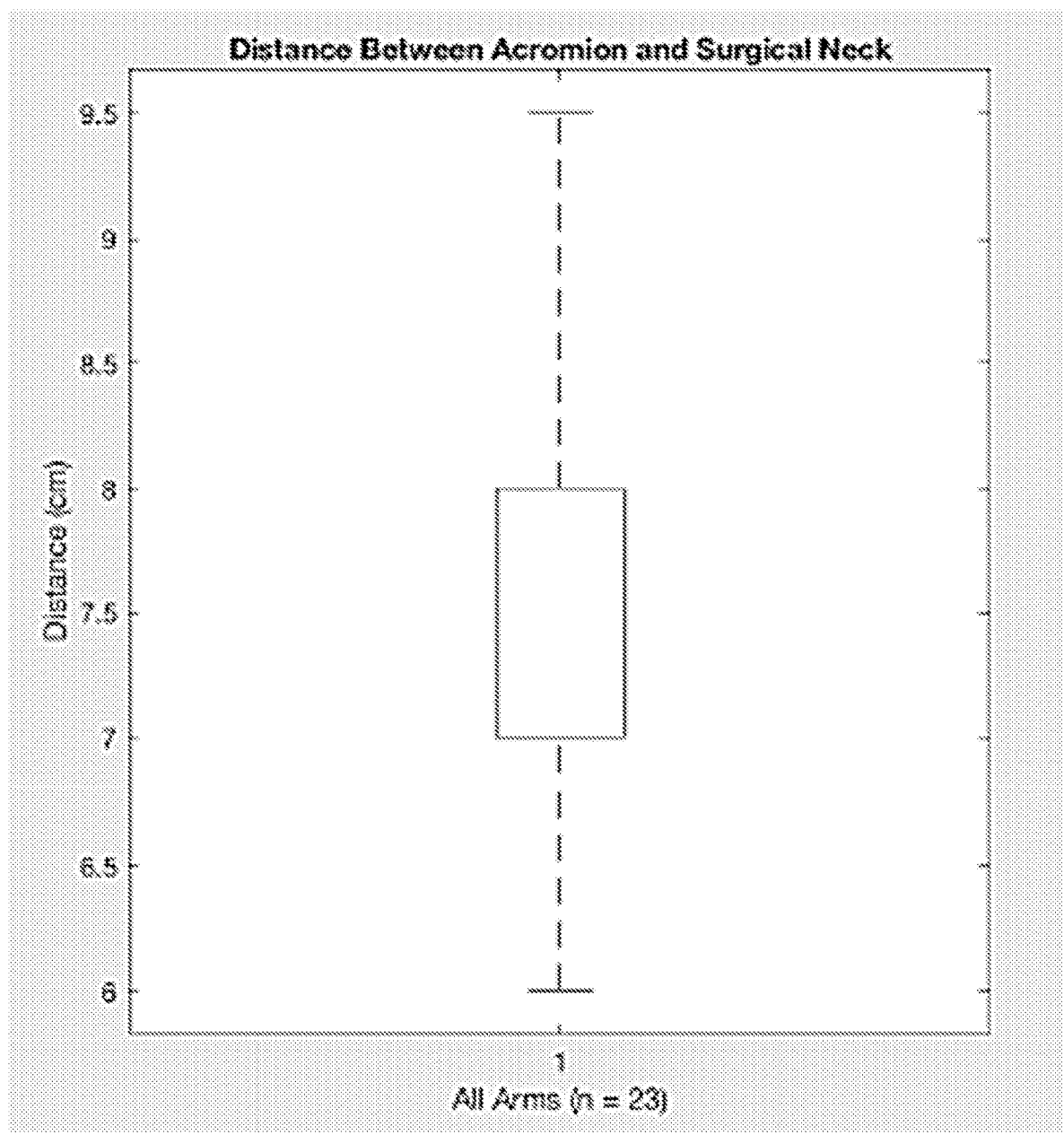
FIG. 11 illustrates a range of distances in human shoulders from the acromion of the scapula to the surgical neck of the humerus.

In order to understand the effects of the soft tissue present in the shoulder, measurements were taken on 23 cadavers. In this case, the measurement extended from the acromion (the bony protrusion on the top of the shoulder) to the surgical neck. The acromion was chosen as an appropriate landmark, since it is palpable across almost all patients, even those with increased muscle and adipose tissue. The variation in these measurements was found to be within 3.5 centimeters (see FIGS. 9 and 11), an increase which was expected since the measurement traced the outer surface of the arm and was affected by the amount of soft tissue. However, this variation is still minor enough for guide 100 to accurately indicate an insertion site for intraosseous infusion through guide 100 to the target region.

In an embodiment, guide 100 is configured such that insertion-site indication holes 110 indicate insertion sites for IO infusion to a target region that is superior of surgical neck of the humerus, inferior the subdeltoid bursa and muscle insertion sites, and lateral to the bicipital groove. For example, the target region may be superior of surgical neck of the humerus by a distance that is between 0.5 and 2.5 centimeters, or within 25% of 1.5 centimeters.

The distance 182 (see FIG. 1C) between alignment hole 120 and insertion-site indication holes 110, projected onto plane 180 is set to ensure that insertion-site indication holes 110 line up with the target region when alignment hole 120 is aligned over the acromion. In one implementation, distance 182 matches the distance from the acromion to the target region for a typical patient. For example, as based on the data of FIG. 9 and an example target region position 1.5 centimeters superior to the surgical neck, distance 182 may be in the range between 4.5 and 7.5 centimeters.

In one embodiment, each insertion-site indication hole 110 is approximately circular and has a diameter that is between 1.5 and 2.5 centimeters. In embodiments, each insertion-site indication hole 110 is fully surrounded by material of the guide. This size is suitable for accommodating a semi-automatic IO device, such as the EZ-IO Intraosseous Vascular Access System (Teleflex, Morrisville, N.C.). In another embodiment, the shape of each insertion-site indication hole 110 deviates from circularity and has a smallest dimension of at least 1.5 centimeters. In this embodiment, each insertion-site indication hole 110 may have a largest dimension of 2.5 centimeters or less.

Figure 12:
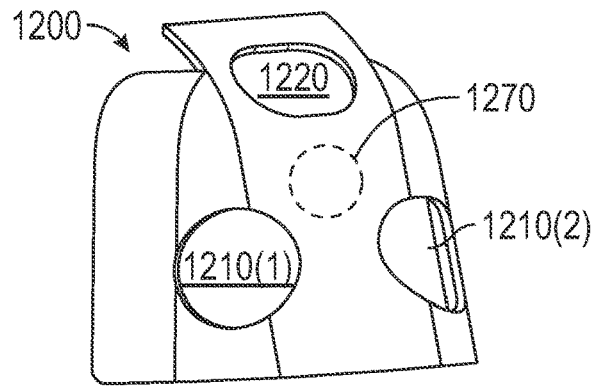
FIGS. 12, 13, and 14 are perspective views of an embodiment of the humeral guide for intraosseous infusion.

FIG. 12 shows one bilateral humeral guide 1200 for IO infusion. Guide 1200 is an embodiment of guide 100 and forms an alignment hole 1220 and two insertion-site indication holes 1210. For ease of handling, guide 1200 may be equipped with a handle. Such a handle may be affixed to the guide 1200 in a region 1270, or integrally formed with the remainder of guide 1200 and extending in a lateral or lateral-inferior direction from region 1270.

Figure 13:
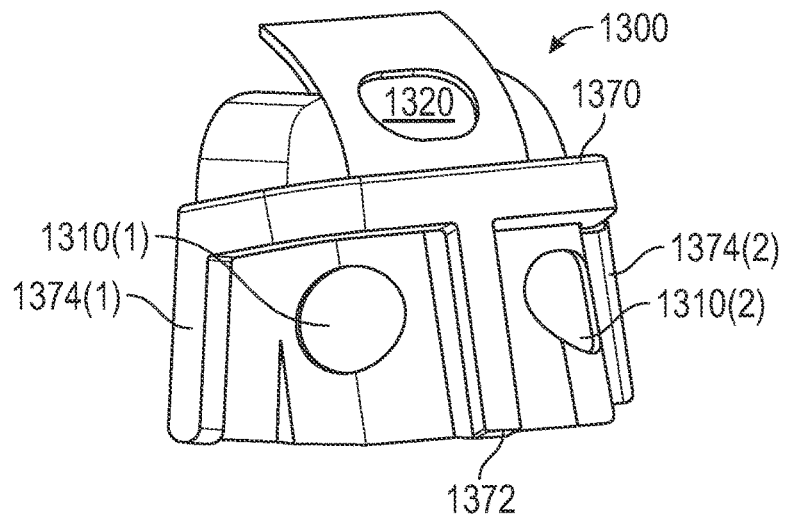

FIG. 13 shows one bilateral humeral guide 1300, for IO infusion, which has raised ridges that may be used as handles. Guide 1300 is an embodiment of guide 100 and forms an alignment hole 1320 and two insertion-site indication holes 1310. Guide 1300 has (a) a central raised ridge 1372 between insertion-site indication holes 1310 in the region of guide 1300 corresponding to side portion 140, (b) a medial raised ridge 1374(1) at or near the medial edge of each of the regions of guide 1300 corresponding to front-back portions 150, and (c) an upper raised ridge 1370 that connects a top end of central raised ridge 1372 to a top end of each medial raised ridge 1374. Without departing from the scope hereof, one or more raised ridges (or portions thereof) shown in FIG. 13 may be omitted from guide 1300. For example, guide 1300 may be provided with only central raised ridge 1372 or with only central raised ridge 1372 and upper raised ridge 1370 (or a central portion thereof).

The raised ridges of guide 1300, especially upper raised ridge 1370, may reduce the flexibility of guide 1300 as compared to that of guide 1200. This may reduce the ability of guide 1300 to conform to different shoulder sizes and shapes. However, the handling functionality provided by the raised ridges (or potential liability issues associated with a handle-less guide) may outweigh flexibility concerns.

Figure 14:
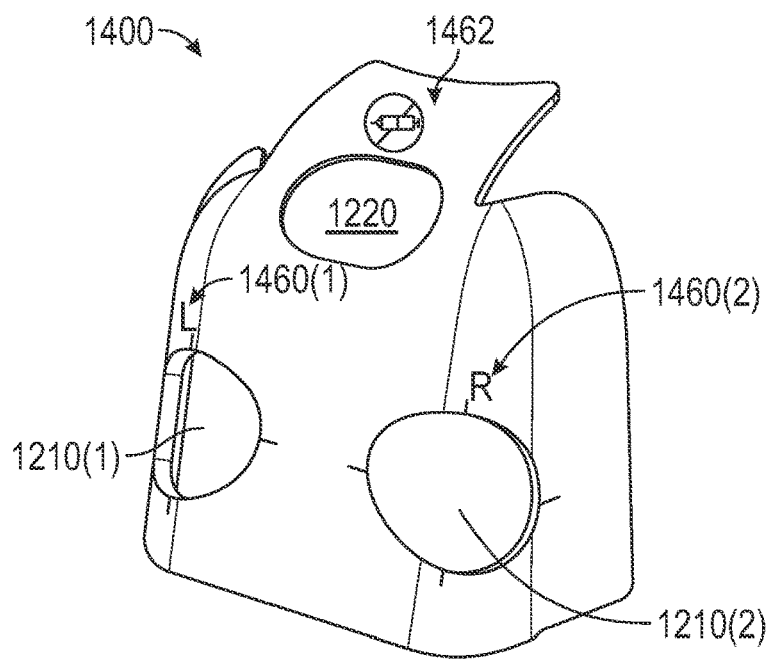

FIG. 14 shows one bilateral humeral guide 1400, for IO infusion, with markings to aid a user. Guide 1400 is a modification of guide 1200, which further includes markings. Guide 1300 may be modified in a similar fashion to include similar markings. Guide 1200 includes one or both of (a) a marking 1460(1) adjacent insertion-site indication hole 1210(1) indicating that insertion-site indication holes 1210(1) is intended for use on the left shoulder, and a marking 1460(2) adjacent insertion-site indication hole 1210(2) indicating that insertion-site indication holes 1210(2) is intended for use on the right shoulder, and (b) a marking 1462 at alignment hole 1220 indicating that alignment hole 1220 is not intended for needle/drill insertion.

Markings 1460(1) and 1460(2) may be "L" and "R", respectively, as shown in FIG. 14. However, other versions of markings 1460 may be used as well (e.g., "left" and "right", or left/right indications in other languages than English). In FIG. 14, marking 1462 is a symbol indicating that no syringe-style devices are allowed. However, other symbols/writings may be used that convey a similar message.

Several, differently-sized guides 100 may be provided as a kit. The size of each guide 100 of such a kit is optimized to fit a corresponding range of shoulder/upper arm sizes. A kit having several such sizes of guides may be particularly useful for less-flexible embodiments of guide 100, such as guide 1300. In order to determine the number of cup sizes necessary to fit 90% of individuals, an assembly made of a humerus, scapula, partial clavicle, torso, EZ IO drill, and the guide was created in SolidWorks. The bones were imported as 3D scans of a Sawbones model. The arm silhouette was modeled using measurements of axillary arm circumference taken from a large-scale anthropometric study. In order to determine the range of guide size, the axillary arm circumference was incrementally adjusted and guide fit was visually assessed. Once the arm became too large for the guide to fit comfortably, that axillary arm circumference became the guide size cutoff and the guide was scaled up. The arm was presumed to be an ellipse that is concentric with the humerus; the guide was assumed to have minimal flex. A normal curve for axillary arm circumference is plotted in FIG. 15.

Figure 15:
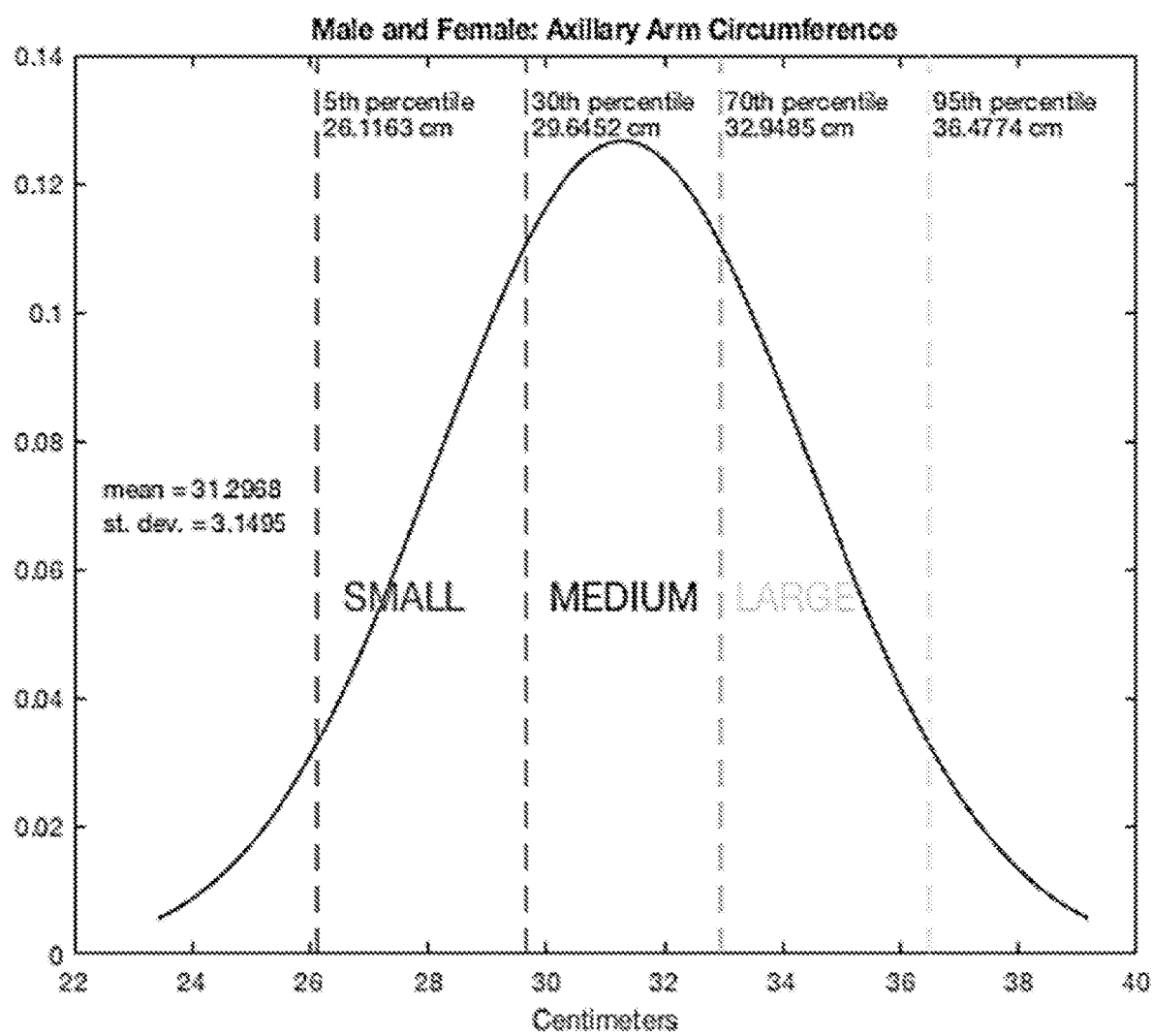
FIG. 15 illustrates a distribution of axillary arm circumference of multiple human upper arms.
Figure 16:
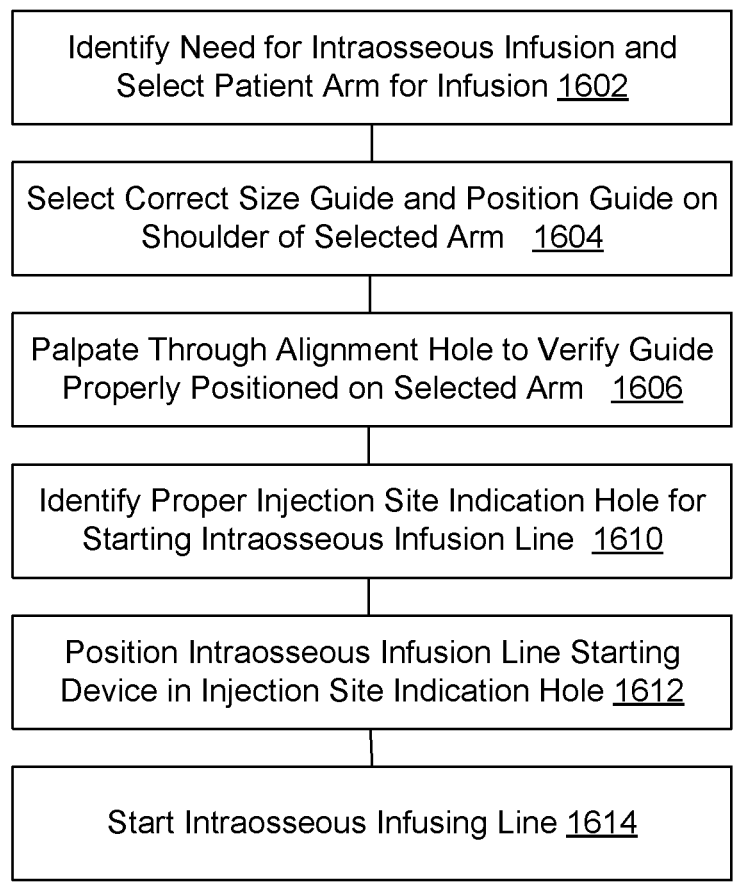
FIG. 16 is a flowchart of a method of starting an intraosseous infusion line using the device of FIG. 1A, 1B, 1C, 12, 13, or 14.

To summarize, the guide 100 is used according to the method of starting a line for intraosseous infusion illustrated in FIG. 16. First, need for an intraosseous infusion in a patient is identified 1602, and an arm—preferably an uninjured arm—of the patient is selected for the interosseous infusion line. A guide 100 is selected according to arm circumference from the kit of small, medium, and large guides discussed with reference to FIG. 15 and positioned 1604 over the shoulder and upper arm of the patient, and correct position of the guide is verified 1606 by palpation of the acromion through the acromion verification or alignment hole 120 of the guide. The correct insertion site indication hole 110(1) for the left arm or 110(2) for the right arm is identified 1610 of the two insertion-site indication holes of the guide, and an intraosseous infusion starting device is positioned 1612 in the correct insertion site indication hole. The intraosseous infusion starting device, such as the EZ-IO although other intraosseous infusion starting devices may be used, is then used according to its manufacturer's instructions to drill into the humerus of the patient and start 1614 the intraosseous infusion line.

Informed by this study, one kit includes three different guides 100 (for example guides 1300) in respective sizes small, medium, and large (see sizes indicated in FIG. 15). Each cup size fits a range of about 3.5 centimeters in axillary arm circumference. All three sizes have identical hole dimensions but differ in width so as to fit different arm sizes.

Combinations

The guide herein described has various features that may be combined in various ways. Combinations of features anticipated by the inventors include:

A bilateral humeral guide designated A for intraosseous infusion includes a three-dimensional mirror symmetric shell configured to fit on either shoulder of a patient, the shell being symmetric about a plane bisecting an alignment hole configured to aid positioning of the shell on the shoulder by aligning the alignment hole on acromion of the shoulder, and two insertion-site indication holes symmetrically positioned on two opposite sides of the plane, the insertion-site indication holes including a left and a right hole each configured to indicate insertion sites for intraosseous infusion through the shell to a target region of a left or right humerus of the patient when the shell is positioned on the shoulder corresponding to the respective humerus.

A guide designated AA including the guide designated A, a first one of the insertion-site indication holes being configured to provide access, from an anterior-lateral direction to a target region of the left humerus of the patient when the shell is fit on the left shoulder with the alignment hole over acromion of the left shoulder, a second one of the insertion-site indication holes being configured to provide access, from an anterior-lateral direction to the target region of a right humerus of the patient when the shell is fit on the right shoulder with the alignment hole over the acromion of the right shoulder.

A guide designated AB including the guide designated A or AA, and including a first marking on the shell adjacent the first one of the insertion-site indication holes indicating that the first one of the insertion-site indication holes is intended for use on the left shoulder; and a second marking on the shell adjacent the second one of the insertion-site indication holes indicating that the second one of the insertion-site indication holes is intended for use on the right shoulder.

A guide designated AC including the guide designated A, AA, or AB, and further including a first marking on the shell at the alignment hole indicating that the alignment hole is not intended for insertion of an intraosseous infusion device.

A guide designated AD including the guide designated A, AA, AB, or AC, the target regions being superior of a surgical neck of the respective humerus, inferior a subdeltoid bursa and muscle insertion sites, and lateral to a bicipital groove of the humerus.

A guide designated AE including the guide designated A, AA, AB, AC, or AD, the indicated target region being superior of a surgical neck of the humerus by a distance that is between 0.5 and 2.5 centimeters.

A guide designated AF including the guide designated A, AA, AB, AC, AD, or AE, each of the insertion-site indication holes having a smallest dimension of at least 1.5 centimeters.

A guide designated AG including the guide designated A, AA, AB, AC, AD, AE, or AF each of the insertion-site indication holes having a largest dimension of no more than 2.5 centimeters.

A guide designated AH including the guide designated A, AA, AB, AC, AD, AE, AF, or AG, the shell including: a top portion bisected by the first plane configured to fit on top of the shoulder; a side portion extending from the top portion, bisected by the first plane and configured to fit against a lateral side of an upper arm of the patient; and two front-back portions extending from the side portion on two respective opposite sides of the first plane, forming a mirror image of each other with respect to reflection in the first plane, each of the front-back portions and configured to extend in medial direction from the side portion.

A guide designated AJ including the guide designated, each of the insertion-site indication holes being at transition between the side portion and a respective one of the front-back portions.

A guide designated AK including the guide designated AH or AJ the top portion being (i) directly connected to the side portion and (ii) connected to the front-back portions only indirectly via the side portion.

A guide designated AL including the guide designated AH, AJ, or AK the shell further forming at least one raised ridge.

A guide designated AM including the guide designated AH, AJ, AK, or AL the shell further forming: a central raised ridge on the side portion along at least part of intersection between the side portion and the first plane; on each of the front-back portions, a medial raised ridge along edge of the front-back portion farthest from the side portion; and an upper raised ridge connecting a top end of the central raised ridge to a top end of each medial raised ridge.

A guide designated AN including the guide designated AH, AJ, AK, AL, or AM the front-back portions being non-parallel, distance between the front-back portions increasing with (i) distance from the side portion and (ii) distance from the top portion, the top portion being at an oblique angle to the side portion.

A guide designated AO including the guide designated A, AA, AB, AC, AD, AE, AF, AG, AH, AJ, AK, AL, AM, or AN, the shell being flexible so as to conform to shoulders having a range of different sizes.

A guide designated AP including the guide designated A, AA, AB, AC, AD, AE, AF, AG, AH, AJ, AK, AL, AM, AN, or AO being injection molded.

A guide designated AQ including the guide designated AP, made of acrylonitrile butadiene styrene, nylon, polycarbonate, polystyrene, or a combination thereof.

A guide designated AR including the guide designated AQ, made of acrylonitrile butadiene styrene.

A guide designated AS including the guide designated, AA, AB, AC, AD, AE, AF, AG, AH, AJ, AK, AL, AM, AN, AO, AP, AQ, or AR, each of the alignment hole and the insertion-site indication holes being fully surrounded by material of the shell.

A method of starting a line for intraosseous infusion designated B includes: identifying need for intraosseous infusion in a patient, selecting an arm of the patient for starting an interosseous infusion line, positioning the guide AA, AB, AC, AD, AE, AF, AG, AH, AJ, AK, AL, AM, AN, AO, AP, AQ, or AR on a shoulder of the selected arm of the patient, palpating through alignment hole an acromion of the shoulder of the selected arm of the patient to verify correct alignment of the guide, identifying a correct insertion site indication hole of the two insertion-site indication holes of the guide, positioning an intraosseous infusion starting device in the correct insertion site indication hole, and starting the line for intraosseous infusion.

Changes may be made in the above systems and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present systems and methods, which, as a matter of language, might be said to fall therebetween.

What is claimed is:

1. A bilateral humeral guide for intraosseous infusion, comprising:
a three-dimensional shell that is mirror symmetric with respect to reflection in a first plane and configured to fit on either shoulder of a patient, the shell having:
(a) an alignment hole bisected by the first plane and configured to aid positioning of the shell on the shoulder by aligning the alignment hole on an acromion of the shoulder, and
(b) two insertion-site indication holes symmetrically positioned on two opposite sides, respectively, of the first plane, each of the insertion-site indication holes being configured to indicate insertion sites for intraosseous infusion through the shell to a target region of a respective humerus of the patient when the shell is fit on the shoulder corresponding to the respective humerus;
the shell including:
a top portion bisected by the first plane configured to fit on top of the shoulder;
a side portion extending from the top portion, bisected by the first plane and configured to fit against a lateral side of an upper arm of the shoulder of the patient; and
two front-back portions extending from the side portion on two respective opposite sides of the first plane, forming a mirror image of each other with respect to reflection in the first plane, each of the front-back portions configured to extend in a medial direction from the side portion;
the shell further forming:
a central raised ridge on the side portion along at least part of an intersection between the side portion and the first plane;
on each of the front-back portions, a medial raised ridge along an edge of the front-back portion farthest from the side portion; and
an upper raised ridge connecting a top end of the central raised ridge to a top end of each medial raised ridge.

2. The guide of claim 1, further comprising:
a first marking on the shell adjacent the first one of the insertion-site indication holes indicating that the first one of the insertion-site indication holes is intended for use on the left shoulder; and
a second marking on the shell adjacent the second one of the insertion-site indication holes indicating that the second one of the insertion-site indication holes is intended for use on the right shoulder.

3. The guide of claim 1, further comprising:
a first marking on the shell at the alignment hole indicating that the alignment hole is not intended for insertion of an intraosseous infusion device.

4. The guide of claim 1, the target region being superior of a surgical neck of the respective humerus, inferior a subdeltoid bursa and muscle insertion sites, and lateral to a bicipital groove of the respective humerus.

5. The guide of claim 1, the target region being superior of a surgical neck of the humerus by a distance that is between 0.5 and 2.5 centimeters.

6. The guide of claim 1, each of the insertion-site indication holes having a smallest dimension of at least 1.5 centimeters.

7. The guide of claim 6, each of the insertion-site indication holes having a largest dimension of no more than 2.5 centimeters.

8. The guide of claim 1, each of the insertion-site indication holes being at a transition between the side portion and a respective one of the front-back portions.

9. The guide of claim 1, the top portion being (i) directly connected to the side portion and (ii) connected to the front-back portions only indirectly via the side portion.

10. The guide of claim 1, the front-back portions being non-parallel, wherein a distance between the front-back portions increasing with (i) a distance from the side portion and (ii) a distance from the top portion, and the top portion being at an oblique angle to the side portion.

11. The guide of claim 1, the shell being flexible so as to conform to shoulders having a range of different sizes.

12. The guide of claim 1, the guide being injection molded.

13. The guide of claim 12, the guide being made of acrylonitrile butadiene styrene, nylon, polycarbonate, polystyrene, or a combination thereof.

14. The guide of claim 13, the guide being made of acrylonitrile butadiene styrene.

15. The guide of claim 1, each of the alignment hole and the insertion-site indication holes being fully surrounded by material of the shell.

16. A method of starting a line for intraosseous infusion comprising:
- identifying need for intraosseous infusion in a patient,
- selecting an arm of the patient for starting an interosseous infusion line,
- positioning the guide of claim 13 on a shoulder of the selected arm of the patient,
- palpating, through the alignment hole, the acromion of the shoulder of the selected arm of the patient to verify correct alignment of the guide,
- identifying a correct insertion site indication hole of the two insertion-site indication holes of the guide,
- positioning an intraosseous infusion starting device in the correct insertion site indication hole, and
- starting the line for intraosseous infusion.

* * * * *